United States Patent [19]

Ito

[11] Patent Number: 5,233,519
[45] Date of Patent: Aug. 3, 1993

[54] RADIATION IMAGE DIAGNOSTIC APPARATUS

[75] Inventor: Wataru Ito, Kanagawa, Japan

[73] Assignee: Fuji Photo Film Co., Ltd., Kanagawa, Japan

[21] Appl. No.: 543,306

[22] Filed: Jun. 26, 1990

[30] Foreign Application Priority Data

Jun. 26, 1989 [JP] Japan .................................. 1-162910

[51] Int. Cl.$^5$ ........................ G06F 15/42; G06F 15/62
[52] U.S. Cl. .................................. 364/413.22; 382/54
[58] Field of Search ...................... 364/413.22, 413.13, 364/413.14; 382/6, 54; 358/111; 378/62

[56] References Cited

U.S. PATENT DOCUMENTS

| | | | |
|---|---|---|---|
| 4,258,264 | 3/1981 | Kotera et al. | 250/484 |
| 4,315,318 | 2/1982 | Kato et al. | 364/515 |
| 4,387,428 | 6/1983 | Ishida et al. | 364/414 |
| 4,839,807 | 6/1989 | Doi et al. | 382/6 |
| 5,086,392 | 2/1992 | Nakajima | 364/413.22 |

FOREIGN PATENT DOCUMENTS 56-11395  2/1981  Japan .
56-12599  2/1981  Japan .
61-5193   2/1986  Japan .

Primary Examiner—Robert A. Weinhardt
Assistant Examiner—Ari M. Bai
Attorney, Agent, or Firm—Sughrue, Mion, Zinn, Macpeak & Seas

[57] ABSTRACT

A first display system displays a radiation image, and a region of the radiation image displayed by the first display system is designated. A number of images of abnormalities which appeared in the past radiation images have been stored in a memory and the correlations between the image in the designated region of the radiation image displayed by the first display system and the respective images of abnormalities stored in the memory are calculated. An image of abnormality having a high correlation with the image in the designated region is extracted from the stored images of abnormalities, and a second display system displays image of abnormality extracted.

6 Claims, 1 Drawing Sheet

RADIATION IMAGE DIAGNOSTIC APPARATUS

BACKGROUND OF THE INVENTION

1. Field of the Invention

This invention relates to a radiation image diagnostic apparatus for reproducing and displaying a radiation image of an object on a display device.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, as disclosed in Japanese Patent Publication No. 61(1986)-5193, an X-ray image is recorded on an X-ray film having a small gamma value chosen according to the type of image processing to be carried out, the X-ray image is read out from the X-ray film and converted into an electric signal (image signal), and the image signal is processed and then used for reproducing the X-ray image as a visible image on a copy photograph or the like. In this manner, a visible image having good image quality with high contrast, high sharpness, low graininess, or the like can be reproduced.

Also, when certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal. The image signal is then used to reproduce the radiation image of the object as a visible image on a recording material such as photographic film, on a display device such as a cathode ray tube (CRT), or the like.

Radiation image recording and reproducing systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light which the stimulable phosphor sheet emits when being stimulated varies over a wide range and is proportional to the amount of energy stored thereon during its exposure to the radiation, it is possible to obtain an image having a desirable density regardless of the energy intensity of the radiation to which the stimulable phosphor sheet was exposed. In order to obtain the desired image density, an appropriate read-out gain is set when the emitted light is being detected and converted into an electric signal to be used in the reproduction of a visible image on a recording material, such as photographic film, or on a display device, such as a CRT.

When a radiation image containing therein an image which can be an image of an abnormality is reproduced, for instance, on a CRT as a visible image in the aforesaid systems using an X-ray film or a stimulable phosphor sheet, sometimes it is difficult to determine what the abnormality is. In order to overcome such difficulties, there has been proposed, in U.S. patent application Ser. No. 260,349, a radiation image diagnostic apparatus in which a reference image can be displayed together side by side with the radiation image to be viewed. Further, in the patent publication, there is disclosed a radiation image diagnostic apparatus which, when viewing an X-ray image of the chest containing therein an image of pneumoconiosis, automatically selects a reference X-ray image which is the most similar to the X-ray image to be viewed from a number of reference X-ray images and displays the most similar reference X-ray image together with the X-ray image to be viewed.

However, it is very difficult to select the most similar reference X-ray image with a high accuracy except the case where the image of the abnormality to be viewed clearly appears over a wide range of the X-ray image like pneumoconiosis or where the purpose of the diagnosis is limited in advance to a particular abnormality such as pneumoconiosis. Accordingly, when it is difficult to determine the kind of abnormality whose image is contained in the X-ray image while what abnormality is contained in the X-ray image to be viewed has not been informed in advance, it is necessary to display in sequence X-ray images containing therein images of various abnormalities whose kinds have been known side by side with the X-ray image to be viewed.

SUMMARY OF THE INVENTION

In view of the foregoing observations and description, the primary object of the present invention is to provide a radiation image diagnostic apparatus which can accurately select reference radiation images having close relevance to the radiation image to be viewed and can display them together with the radiation image to be viewed even if the radiation image contains an image of abnormality in only a limited part thereof and even in the case where a plurality of diseases are to be diagnosed at one time.

The radiation image diagnostic apparatus in accordance with the present invention comprises a first display means which displays a radiation image, a designating means which designates a region of the radiation image displayed by the first display means, a storage means which storages a number of images of abnormalities which appeared in the past radiation images, a calculating means which calculates the correlations between the image in the designated region of the radiation image displayed by the first display means and the respective images of abnormalities stored in the storage means and extracts from the stored images of abnormalities an image of abnormality having a high correlation with the image in the designated region, and a second display means which displays image of abnormality extracted by the calculating means.

The "image of abnormality" denotes an image which cannot be found in a standard radiation image, e.g., an image of a tumor, calcification, incrassation of the pleura, pneumothorax or the like which can be found in a chest X-ray image. It is not necessary that all of those abnormalities are the subject of diagnosis and only one or more of those abnormalities may be the subject of diagnosis.

The second display means may display, as a reference radiation image, the image of abnormality extracted by the calculating means by itself or the radiation image containing therein the image of abnormality extracted by the calculating means. Further, instead of displaying the image of abnormality extracted by the calculating means by itself or the radiation image containing therein the image of abnormality extracted by the calculating means, the second display means may display characters, codes, symbols or the like which represent the kind of disease and/or the degree of progress of the disease. In this specification, the expression "display image of abnormality extracted by the calculating means" should be broadly interpreted to include all the manners of display described above.

The first and second display means may be separately provided and disposed adjacent to each other. For example, the first and second display means may be a pair of CRT display systems which are disposed adjacent to each other. Further, the first display means may be a half of a single screen of a CRT display system and the second display means may be the other half of the screen.

Said correlation may be obtained by various methods of calculation and need not be limited to values obtained by a particular method of calculation. For example, the correlation may be calculated on the basis of the degree of similarity in shape, density and/or the like between the image in the designated region of the radiation image displayed by the first display means and the respective images of abnormalities stored in the storage means.

Unlike the radiation image diagnostic apparatus disclosed in U.S. patent application Ser. No. 260,349 in which numbers of whole radiation images are stored as the reference radiation images, in the radiation image diagnostic apparatus in accordance with the present invention, numbers of images of abnormalities which were found in numbers of radiation images are stored and the correlations are between the image in the designated region of the radiation image displayed by the first display means and the respective images of abnormalities stored in the storage means. Accordingly, in accordance with the present invention, the most similar reference radiation image can be selected with a high accuracy and is displayed together with the radiation image to be viewed even if the radiation image contains an image of abnormality in only a limited part thereof and even in the case where a plurality of diseases are to be diagnosed at one time.

DESCRIPTION OF THE PREFERRED EMBODIMENT

Figure 2:
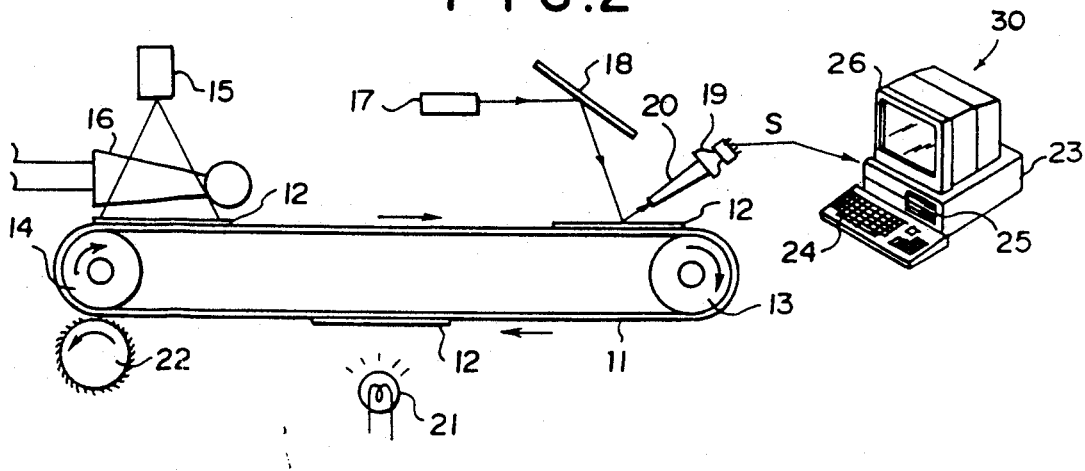
FIG. 2 is a view which more concretely shows the radiation image diagnostic apparatus in combination with a radiation image recording and read-out apparatus which inputs radiation image signals to the radiation image diagnostic apparatus.

FIG. 2 shows a radiation image diagnostic apparatus in accordance with an embodiment of the present invention together with a radiation image recording and read-out apparatus for obtaining the radiation image signal to be transferred to the radiation image diagnostic apparatus. The radiation image recording and read-out apparatus utilizes the stimulable phosphor sheet.

In FIG. 2, three stimulable phosphor sheets 12 are secured in equally spaced relation on an endless belt conveyor 11. The conveyor 11 to which the stimulable phosphor sheets 12 are secured is engaged with a driving roller 13 and a driven roller 14, and moved in the direction as indicated by the arrow by the driving roller 13 which is rotated by a driving unit (not shown). In the vicinity of the driven roller 14 is disposed a radiation source 15 to face the conveyor 11. The radiation source 15 may be an X-ray source or the like, and projects a radiation image of an object 16 positioned between the stimulable phosphor sheets 12 and the radiation source 15 onto the stimulable phosphor sheets 12. In the vicinity of the driving roller 13 are disposed a stimulating ray source 17 for producing stimulating rays such as a laser beam, a light deflector 18 constituted by a galvanometer mirror or the like for deflecting the stimulating rays produced by the stimulating ray source 17 in the width direction of the conveyor 11, and a photodetector 19 for reading out the light emitted by the stimulable phosphor sheets 12 upon stimulation thereof by the stimulating rays. The photodetector 19 may be constituted by a head-on type photomultiplier, a photoelectric amplification channel plate or the like. The photodetector detects the light emitted by the stimulable phosphor sheets 12 and guided by a light guide member 20. An erasing light source 21 is disposed facing the conveyor 11 on the side opposite to the radiation source 15, the stimulating ray source 17 and the photodetector 19. The erasing light source 21 produces light having a wavelength within the stimulating wavelength range of the stimulable phosphor sheets 12 irradiated onto the sheets 12 to cause them to release the radiation energy stored thereon. The erasing light source 21 may be constituted by, e.g., a tungsten-filament lamp, a halogen lamp, an infrared lamp, or a laser source as disclosed in U.S. Pat. No. 4,400,619. Since the radiation energy stored on the stimulable phosphor sheets 12 can also be eliminated by heating them as disclosed in, for example, Japanese Unexamined Patent Publication No. 56(1981)-12599, the erasing light source 21 may be replaced by a heating means. A cylindrical cleaning roller 22 is opposed to the driven roller 14 with the conveyor 11 intervening therebetween. The cleaning roller 22 is rotated in the counterclockwise direction as seen in FIG. 2 by a drive unit (not shown), and removes dust from the surfaces of the sheets 12 moving in contact with the cleaning roller 22. If necessary, the cleaning roller 22 may be on an electrostatic attraction type which collects dust or the like by an electrostatic force.

The light guide member 20 may be of a material and a construction as disclosed in U.S. Pat. Nos. 4,346,265 and 4,369,367, and Japanese Unexamined Patent Publication No. 56(1981)-11395, and may be used by the method as disclosed therein.

Figure 1:
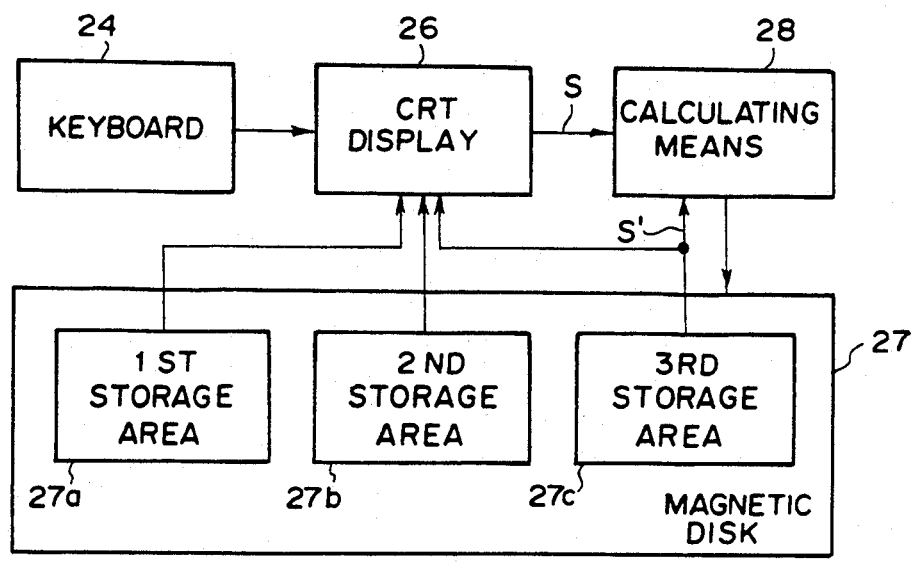
FIG. 1 is a view which schematically shows the arrangement of a radiation image diagnostic apparatus in accordance with an embodiment of the present invention.

The radiation image recording and read-out apparatus having the aforesaid configuration is operated as follows. The conveyor 11 is intermittently moved by the distance corresponding to one-third of the entire length thereof at a time by the driving roller 13. The stopping position of the conveyor 11 is adjusted so that one stimulable phosphor sheet 12 faces the radiation source 15 when the conveyor 11 stops. When the conveyor 11 is stopped, the radiation source 15 is turned on to cause the sheet 12 facing the radiation source 15 to store the radiation image of the object 16. After the radiation image is recorded on the sheet 12, the conveyor 11 is further moved by the distance of one-third the conveyor length and stopped. At this time, the sheet 12 carrying thereon the radiation image is stopped in the position facing the light deflector 18 and the photodetector 19, and scanned with the stimulating rays produced by the stimulating ray source 17. Scanning conducted in the width direction of the conveyor 11 (main scanning) by the light deflector 18, and also in the length direction of the conveyor 11 (sub-scanning) by the movement of a stage carrying the stimulating ray source 17, the light deflector 18, the photodetector 19 and the light guide member 20 in the length direction of the conveyor 11. The stage can be easily formed by use of a known linear movement mechanism. Upon exposure to the stimulating rays, the sheet 12 emits light in proportion to the stored radiation energy. The emitted light enters the photodetector 19 via the light guide member 20, and a radiation image signal S corresponding to the radiation image stored on the sheet 12 is generated by the photodetector 19. The radiation image signal S is fed to a radiation image diagnostic apparatus 30. The radiation image diagnostic apparatus 30 comprises a main body 23 having built-in CPU and memory, a CRT display system 26 which displays a visible image on the basis of the radiation image signal S or other required information, a keyboard 24 for inputting other information required by the radiation image diagnostic apparatus 30, and a disk drive 25 for driving a magnetic disk 27 (FIG. 1). The radiation image signal S fed to the radiation image diagnostic apparatus 30 is subjected to necessary image processing in accordance with an instruction specified by the keyboard 24, and the processed image signal is stored in a first storage area 27a (FIG. 1) of the magnetic disk 27. The name of the object of the radiation image signal S read out in the manner described above, the date of recording, and other ID information for identifying the radiation image signal S are input by the keyboard 24, and are stored in a second storage area 27b of the magnetic disk 27. After the radiation image is thus read out, the conveyor 11 is further moved by the distance of one-third the length thereof and stopped. In this condition, the stimulable phosphor sheet 12 from which the radiation image has been read out is opposed to the erasing light source 21, and exposed to the erasing light produced thereby to eliminate the radiation energy of the radiation image remaining on the sheet 12 after the read-out step, the radiation emitted by radioactive isotopes such as Ra226 and K40 existing in trace amounts in the stimulable phosphor, and environmental radiations stored in the stimulable phosphor. In this manner, the stimulable phosphor sheet 12 is recovered to the condition reusable for further image recording. Thereafter, the conveyor 11 is moved by the distance of one-third the conveyor length until the erased sheet 12 faces the radiation source 15. Midway during this movement, dust on the surface of the sheet 12 is removed by the cleaning roller 22. The sheet 12 free from any radiation energy and dust is reused to record a radiation image at the radiation source 15.

The radiation image recording and read-out apparatus is not limited to the apparatus using the stimulable phosphor sheet and may, for instance, be an apparatus for recording an X-ray image on a conventional X-ray photographic film and then reading out the X-ray image by scanning the X-ray photographic film.

In FIG. 1, radiation image signals S and ID information signals for identifying the respective radiation image signals S are once stored respectively in the first and second storage areas 27a and 27b of the magnetic disk 27, and then read out to the CRT display system 26. The CRT display system 26 displays the radiation image represented by the radiation image signal S together with the ID information for the radiation image. The CRT display system 26 functions both as the first display means and the second display means described above.

When the radiation image displayed by the CRT display system 26 contains therein an image of abnormality, the image of abnormality is compared with an image of abnormality which was found in the past radiation image in the following manner.

A number of radiation images which were recorded and read out in the past and contain therein various images of abnormalities are stored in the first storage area 27a of the magnetic disk 27. A number of images of abnormalities extracted from the radiation images stored in the first storage area 27a are stored in a third storage area 27c of the magnetic disk 27. ID information including information for identifying each radiation image and information for identifying the image of abnormality contained in the radiation image (e.g., the name of the disease corresponding to the image of abnormality and/or the degree of progress of the disease) is stored in the second storage area 27b of the magnetic disk 27. The magnetic disk 27 functions as the storage means described above.

A visible image displayed on the screen of the CRT display system 26 on the basis of the radiation image signal S contains an image of abnormality which cannot be found in the normal radiation images, the operator designates a region of the visible image including the image of abnormality by the use of the keyboard 24. In this embodiment, the keyboard 24 functions as the designating means. In this particular embodiment, a rectangular frame is displayed on the screen of the CRT display system 26 together with the visible image, and the rectangular frame is moved on the screen to the position where the image of abnormality is surrounded by the frame. Thus the designation of a region is carried out.

The radiation image signal S representing the image in the designated region is input into a calculating means 28. Further the image signals S' representing the images of abnormalities which have been extracted from the past radiation images and stored in the third storage area 27c of the magnetic disk 27 are input in sequence into the calculating means 28. The CPU and the memory which are built in the main body 23 of the radiation image diagnostic apparatus 30 function as the calculating means 28 and calculates according to the following formula (1). In this embodiment, the image signals S' were extracted from the past radiation images by the use of the same frame as the frame used for designating a region in the visible image, and accordingly, consists of picture elements which are the same in number and the arrangement as those in the designated region in the visible image. The calculating means 28 calculates correlations between the image signal S representing the image in the designated region and the radiation image signals S' which represent various images of abnormalities and are input in sequence into the calculating means 28. In order to obtain the correlations, the dispersion $\sigma^2$ is calculated according to the following formula (1).

$$\sigma^2 = \sum_{i,j}{}_D \{S(i,j) - S'(i,j)\}^2 \quad (1)$$

wherein S(i,j) and S'(i,j) represents the radiation image signals S and S' of a picture element in the designated region and the picture element of the image of abnormality corresponding to the picture element in the designated region, and D represents the designated region. The image of abnormality the dispersion $\sigma^2$ of which is the smallest is regarded as the image of abnormality having the highest correlation with the image in the designated region. Further, i,j D is indicative that the calculation according to formula (1) is carried out within the region D.

After the image of abnormality having the highest correlation with the image in the designated region is thus obtained, the radiation image signal S' representing the radiation image containing therein the image of abnormality and the ID information signal corresponding to the radiation image are respectively read out from the first and second storage areas 27a and 27b of the magnetic disk 27 and input into the CRT display system 26. The CRT display system 26 displays the radiation image and the ID information on the screen together with the radiation image represented by the radiation image signal S.

By designating a region of a radiation image including an image of abnormality and by obtaining the correlation between the image in the designated region and the image (an image of abnormality) in a region of each of the past radiation images stored in the magnetic disk 27, reference radiation images having close relevance to the radiation image to be viewed can be selected with a high accuracy and can be displayed together with the radiation image to be viewed.

The correlations between the image signal S representing the image in the designated region and the radiation image signals S' which represent various images of abnormalities and are input in sequence into the calculating means 28 may be calculated according to various formulae other than formula (1). For example, in one modification, the image in the designated region and the images of abnormalities read out from the magnetic disk 27 are subjected to Fourier transform on the basis of the radiation image signals S and S, whereby Fourier transform image signals F and F' are obtained, and the dispersion $\sigma'^2$ is obtained according to the following formula (2).

$$\sigma'^2 = \int_{f1}\int_{f2}\{F(f1,f2) - F'(f1,f2)\}^2 \quad (2)$$

wherein F(f1,f2) and F'(f1,f2) respectively represent the Fourier transform image signals F and F' of coordinates (f$_1$, f$_2$) in the spatial frequency range of the Fourier transform image signals F and F'. The image of abnormality the dispersion $\sigma'^2$ of which is the smallest is regarded as the image of abnormality having the highest correlation with the image in the designated region. In another modification, histogram of the radiation image signals S representing the image in the designated region (the frequency of each value of the radiation image signal) and histograms of the radiation image signals S' which represent various images of abnormalities and are input in sequence into the calculating means 28 are obtained, and the dispersion $\sigma''^2$ is obtained according to the following formula (3).

$$\sigma''^2 = \int(N_s - N_{s'})^2 \quad (3)$$

wherein $N_s$ and $N_{s'}$ respectively represent the frequencies of the radiation image signals S and S'. The image of abnormality the dispersion $\sigma''^2$ of which is the smallest is regarded as the image of abnormality having the highest correlation with the image in the designated region.

The calculating means 28 may calculate the correlations which represent the degree of similarity in shape, density and/or the like between the image in the designated region of the radiation image displayed by the first display means and the respective images of abnormalities read out from the magnetic disk 27 according to any one of the formulae (1), (2) and (3), or any other known formula, or any combination of the formulae.

I claim:

1. A radiation image diagnostic apparatus comprising:
   a display means for displaying a radiation image;
   a designating means for designating a region of the radiation image displayed by the display means;
   a first storage means for storing a number of images of abnormalities which appeared in previous radiation images;
   a comparing means for comparing the image in the designated region with each of the respective images of abnormalities; and
   a calculating means for calculating the correlation between the image in the designated region of the radiation image displayed by the display means and each of the respective images of abnormalities stored in the first storage means and for extracting from the stored images of abnormalities an image of abnormality having a high correlation with the image in the designated region;
   said display means displaying the image of abnormality extracted by the calculating means.

2. A radiation image diagnostic apparatus as defined in claim 1 further comprising:
   a radiation image recording and read-out apparatus coupled to said display means, said display means displays a radiation image on the basis of a radiation image signal supplied from said radiation image recording and read-out apparatus.

3. A radiation image diagnostic apparatus as defined in claim 2 further comprising:
   a second storage means coupled to said display means, said radiation image signal is supplied to the display means by said second storage means which stores a radiation signal read-out by the radiation image recording and read-out apparatus.

4. A radiation image diagnostic apparatus as defined in claim 3 in which said first and second storage means are in the same storage device in different storage areas thereof, said images of abnormalities being stored in the form of image signals.

5. A radiation image diagnostic apparatus as defined in claim 4 in which said storage device is a magnetic disk.

6. A radiation image diagnostic apparatus as defined in claim 1 in which said display means comprises a CRT display system.

* * * * *